(12) United States Patent
Ertl

(10) Patent No.: US 9,453,722 B2
(45) Date of Patent: Sep. 27, 2016

(54) METHOD AND ARRANGEMENT FOR DETERMINING A COMBINED DATA RECORD FOR A MASTICATORY ORGAN TO BE MEASURED

(75) Inventor: Thomas Ertl, Florstadt (DE)

(73) Assignee: DEGUDENT GMBH, Hanau (DE)

( * ) Notice: Subject to any disclaimer, the term of this patent is extended or adjusted under 35 U.S.C. 154(b) by 565 days.

(21) Appl. No.: 13/392,544

(22) PCT Filed: Aug. 26, 2010

(86) PCT No.: PCT/EP2010/062517
§ 371 (c)(1),
(2), (4) Date: Apr. 25, 2012

(87) PCT Pub. No.: WO2011/023784
PCT Pub. Date: Mar. 3, 2011

(65) Prior Publication Data
US 2012/0224756 A1      Sep. 6, 2012

(30) Foreign Application Priority Data

Aug. 26, 2009   (DE) .................. 10 2009 038 588

(51) Int. Cl.
*G06T 7/00* (2006.01)
*G01B 11/245* (2006.01)
*A61C 9/00* (2006.01)

(52) U.S. Cl.
CPC .............. *G01B 11/245* (2013.01); *A61C 9/00* (2013.01); *A61C 9/0053* (2013.01); *G01B 2210/52* (2013.01)

(58) Field of Classification Search
None
See application file for complete search history.

(56) References Cited

U.S. PATENT DOCUMENTS

| | | | | |
|---|---|---|---|---|
| 2,553,028 A * | 5/1951 | Wright | ................ | 378/170 |
| 4,554,676 A * | 11/1985 | Maldonado et al. | ......... | 378/170 |
| 5,001,738 A * | 3/1991 | Brooks | ................ | 378/170 |
| 5,327,477 A * | 7/1994 | Levy | ................ | 378/168 |
| 5,800,341 A * | 9/1998 | McKenna et al. | ............. | 600/109 |
| 6,190,042 B1* | 2/2001 | Dove et al. | ................ | 378/170 |
| 6,243,439 B1* | 6/2001 | Arai | ............... | A61B 6/032 |
| | | | | 378/162 |
| 6,288,382 B1* | 9/2001 | Ishihara | ................ | 250/201.3 |
| 7,234,937 B2* | 6/2007 | Sachdeva et al. | ............. | 433/24 |
| 7,734,079 B2* | 6/2010 | Hsieh et al. | ................ | 382/131 |
| 7,819,579 B2* | 10/2010 | Schmulenson et al. | ...... | 378/170 |
| 8,087,932 B2* | 1/2012 | Liu | ............... | A61C 7/00 |
| | | | | 382/128 |
| 8,113,829 B2* | 2/2012 | Sachdeva et al. | ............. | 433/24 |
| 8,467,599 B2* | 6/2013 | El Dokor | ................ | 382/159 |

(Continued)

FOREIGN PATENT DOCUMENTS

| DE | 38 10 455 | 10/1989 |
|---|---|---|
| DE | 3810455 A1 | 10/1989 |

(Continued)

*Primary Examiner* — Chan Park
*Assistant Examiner* — Mia M Thomas
(74) *Attorney, Agent, or Firm* — Ladas & Parry LLP

(57) ABSTRACT

A method for determining a combined data record for an object using individual data records based on individual scans of the object, the scans being measured using at least one sensor. To avoid accumulating errors and allow individual data to be rectified or corrected, first partial scans of the object are measured using at least one first sensor and are aligned relative to one another and/or corrected using second partial scans performed by at least two second sensors that are stationary relative to one another, and the individual data records for the combined data record are determined from the aligned and/or corrected partial scans.

22 Claims, 2 Drawing Sheets

(56) References Cited

U.S. PATENT DOCUMENTS

Figure 1:
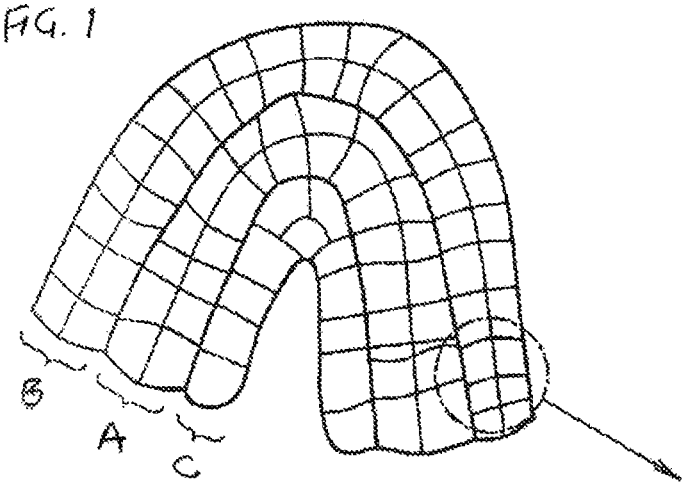

| | | | |
|---|---|---|---|
| 2002/0058229 A1* | 5/2002 | Sugimoto | 433/29 |
| 2003/0012423 A1* | 1/2003 | Boland et al. | 382/154 |
| 2003/0081821 A1* | 5/2003 | Mertelmeier et al. | 382/131 |
| 2003/0194124 A1* | 10/2003 | Suzuki et al. | 382/156 |
| 2003/0219148 A1* | 11/2003 | Scharlack et al. | 382/128 |
| 2004/0142298 A1* | 7/2004 | Taub | A61C 7/00 433/24 |
| 2004/0153283 A1* | 8/2004 | Wargon | 702/156 |
| 2004/0218792 A1* | 11/2004 | Spoonhower et al. | 382/128 |
| 2005/0076914 A1* | 4/2005 | Besharim et al. | 128/207.14 |
| 2005/0153257 A1* | 7/2005 | Durbin et al. | 433/68 |
| 2005/0168742 A1* | 8/2005 | Jung et al. | 356/419 |
| 2005/0192835 A1* | 9/2005 | Kuo | G06F 19/3443 705/2 |
| 2006/0062435 A1* | 3/2006 | Yonaha | 382/118 |
| 2006/0078185 A1* | 4/2006 | Hsieh et al. | 382/131 |
| 2006/0155189 A1* | 7/2006 | Lavallee et al. | 600/426 |
| 2006/0221072 A1* | 10/2006 | Se et al. | 345/420 |
| 2007/0055331 A1* | 3/2007 | Merfeld | 607/116 |
| 2007/0207437 A1* | 9/2007 | Sachdeva et al. | 433/24 |
| 2008/0226150 A1* | 9/2008 | Sadakane | 382/131 |
| 2008/0261168 A1* | 10/2008 | Gutman et al. | 433/69 |
| 2008/0318179 A1* | 12/2008 | Liu | A61C 7/00 433/24 |
| 2009/0092948 A1* | 4/2009 | Gantes | 433/215 |
| 2009/0168953 A1* | 7/2009 | Szommer | 378/38 |
| 2009/0220134 A1* | 9/2009 | Cahill et al. | 382/128 |
| 2010/0074402 A1* | 3/2010 | Bothorel et al. | 378/38 |
| 2010/0075274 A1* | 3/2010 | Klett | 433/56 |
| 2010/0112524 A1* | 5/2010 | Meier | 433/201.1 |
| 2010/0177875 A1* | 7/2010 | Steward et al. | 378/170 |
| 2010/0260405 A1* | 10/2010 | Cinader, Jr. | A61C 7/00 382/131 |
| 2010/0332253 A1* | 12/2010 | Adusimilli et al. | 705/2 |
| 2011/0212418 A1* | 9/2011 | Nakahara et al. | 433/175 |
| 2012/0015316 A1* | 1/2012 | Sachdeva | A61C 19/045 433/24 |
| 2012/0046914 A1* | 2/2012 | Gao | A61C 1/084 703/1 |
| 2012/0092461 A1* | 4/2012 | Fisker | A61B 5/0068 348/46 |
| 2012/0183120 A1* | 7/2012 | Tomoe | 378/39 |
| 2012/0191421 A1* | 7/2012 | Greenberg | 703/1 |
| 2012/0224756 A1* | 9/2012 | Ertl | A61C 9/00 382/131 |
| 2012/0243762 A1* | 9/2012 | Kanerva et al. | 382/131 |
| 2013/0071809 A1* | 3/2013 | Kirkpatrick et al. | 433/29 |
| 2015/0196372 A1* | 7/2015 | Champleboux | 382/128 |
| 2015/0209118 A1* | 7/2015 | Kopelman | A61B 19/54 433/25 |
| 2015/0235104 A1* | 8/2015 | Van Lierde | G06K 9/6215 382/128 |
| 2015/0320320 A1* | 11/2015 | Kopelman | A61B 5/0088 433/24 |

FOREIGN PATENT DOCUMENTS

| | | |
|---|---|---|
| DE | 43 01 538 | 7/1994 |
| DE | 4301538 A1 | 7/1994 |
| DE | 10 2006 013 584 | 9/2007 |
| EP | 2 166 303 | 3/2010 |

* cited by examiner

METHOD AND ARRANGEMENT FOR DETERMINING A COMBINED DATA RECORD FOR A MASTICATORY ORGAN TO BE MEASURED

This application is a 371 of PCT/EP2010/062517 filed on Aug. 26, 2010, which claims priority to German patent application number 10 2009 038 588.6, filed Aug. 26, 2009, which is incorporated herein by reference.

The invention relates to a method for determining a total data set of an object to be measured, which is in the form of a chewing organ or an area thereof, using individual data sets which are based on individual scans of the object, which scans are measured with at least one sensor. The invention also relates to a device for scanning a chewing organ or an area thereof by means of several sensors originating from a holder.

To measure an object three-dimensionally, it is known to scan said object three-dimensionally in order to obtain from the individual data sets a total data set which reproduces the shape of the object to be measured. Said data are required, for example, in dental prosthetics, to produce reconstructions in the CAD/CAM method.

One problem of 3D scanning without fixed relation between individual 3D views is the buildup of an error, which accumulates with increasing individual scan number, during the registration (assembling, matching) of the individual scans to a total data set. To reduce said error, auxiliary parts with known geometry, that is with reference markings, are scanned together with the geometry to be determined.

A device and a method for measuring components are described in DE-A-10 2006 013 584 (U.S. Pat. No. 7,705,929). Here, several triangulation sensors, which are arranged so they can be moved along a displacement path, can originate from a crosspiece.

U.S. Pat. No. 6,288,382 relates to a confocal scanning system provided to measure an object with the aid of a pinhole array.

The present invention is based on the problem of further developing a method and an arrangement of the type mentioned at the start, in such a manner that accumulating errors can be avoided. A rectification or correction of individual data should be possible. In addition, it should also be possible to generate in a simple manner a 3D data set which represents the contour of the object with utmost precision. Furthermore, the device should be easy to handle, so that a chewing organ or a section thereof can be scanned by said device without difficulty.

To solve the problem, the invention substantially provides that, by means of at least one first sensor of a first apparatus, overlapping first partial scans of the object or area thereof are measured; second partial scans of the object or area thereof are measured by at least two second sensors of a second apparatus, which are arranged in a fixed relation; from the first partial scans a total data set which represents the object or the area is calculated, and corrected by means of the second partial scans; or the first partial scans are corrected by means of the second partial scans, and a total data set representing the object or the area is calculated from the corrected partial scans; or, by means of several third sensors arranged in an apparatus in a fixed relation, third partial scans are determined, from the individual data sets of which a total data set representing the object or the area is calculated, wherein, during the measurement, the third sensors can be moved in an uncorrelated manner with respect to the object or the area.

On the basis of the teaching according to the invention, according to the first alternative, 2D or 3D image data or partial scans are determined as first partial scans which overlap, wherein the first partial scans are corrected first by means of the second partial scans determined by the second sensors arranged in a fixed relation to each other, i.e., data are corrected by registration (matching), or, from the first partial scans, a total data set which represents the object to be measured or area thereof is calculated first, in order to then correct the total data set by means of the data obtained from the second sensors which are in a fixed relation. Correcting here comprises a rectification and an alignment. One uses the second partial scans to correct the first partial scans or data thereof, or the total data set calculated from the first partial scans.

The associated method can be combined with the scanning systems known from the prior art, and it can be used to correct errors that occur.

According to the alternative solution proposal, the sensors used for the determination of the total data set are themselves arranged in a fixed relation to each other, so that the partial areas determined by each sensor present an unequivocal assignment, i.e., alignment to each other, and thus a correction or rectification is not necessary. A self-contained scanning system is used, wherein, in particular, all the requirements for a scanning system with regard to the required scanning depth, the required coverage of the object geometry, and the ability to scan objects having an unfavorable aspect ratio, are satisfied.

In particular, it is provided that at least the second and third sensors present single scan optic systems which work preferably according to the principle of multipoint OCT (optical coherence tomography), multipoint confocal imaging or multipoint confocal, with chromatic dispersion.

It is preferred to use a CCD, CMOS, InGaAs or PbS sensor as sensor.

As sensor, a miniature camera in the submillimeter range should be used.

The invention is further characterized in that the optic systems, for example, a miniature camera, required for each sensor can have a confocal design.

At least the second and third sensors in each case originate from a holder which optionally comprises a transparent enveloping cover.

Independently thereof, an electronic system for merging data streams of the sensors as well as a power source should be integrated in the holder, besides the sensors. Said power source can consist of a battery with inductive charging capacity.

The transmission of the data from the holder should preferably be wireless.

The preferred field of use of the teaching according to the invention is the area of 3D scanning of a jaw or jaw area. Therefore, the holder with the elements originating therefrom should be dimensioned in such a manner that an at least partial introduction into a mouth of a patient can occur.

Moreover, at least the third sensors should be arranged on the holder in such a manner that an occlusal, vestibular and platinal/lingual area of at least one area of the chewing organ can be scanned simultaneously.

The invention therefore also relates to a device for scanning a chewing organ or an area thereof by means of several sensors originating from a holder, and it is characterized in that the sensors originate from a holder in which an electronic system for merging data determined with the sensors as well as a power source is integrated. The holder here should present a geometry such that a jaw area to be measured is enclosed, i.e., the occlusal, vestibular and platinal or lingual area should be measurable simultaneously by means of the sensors.

The data that are merged in the electronic system are transmitted preferably in a contactless manner to a processing unit. As electronic system, it is preferred to use a field-programmable gate array (FPGA).

It is preferred that sensors of the same design originate from the holder, although it is also possible to use sensors of different design, depending on the design of the holder. The sensor is particularly a sensor from the group CCD, CMOS, InGaAs, PbS sensor, and miniature camera in the submillimeter range.

Since the measurement is carried out in or on the mouth area, it is further provided that the holder is provided with a transparent enveloping cover which covers at least the sensors. In particular, all the elements originating from the holder are covered by a corresponding enveloping cover.

Moreover, an inertial system can originate from the holder, to measure the position relative to the object to be measured.

Further details, advantages and characteristics of the invention can be obtained not only from the claims, the characteristics—separately and/or in combination—to be obtained from said claims, but also from the following description of preferred embodiment examples to be obtained from the drawing.

Figure 2:
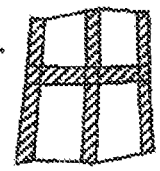
Figure 3:
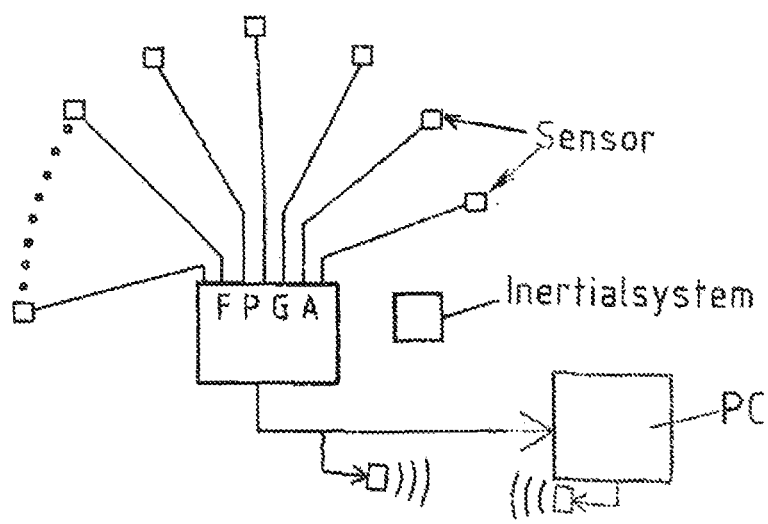
Figure 4:
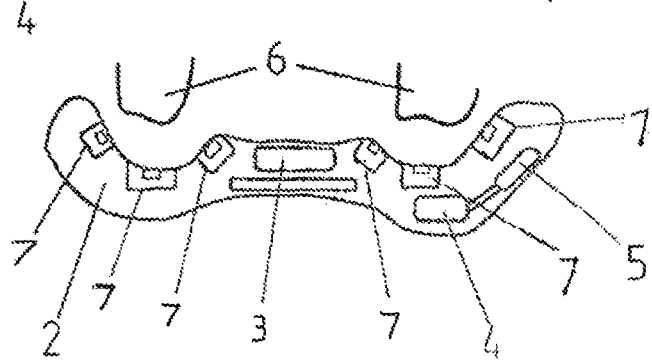
Figure 5:
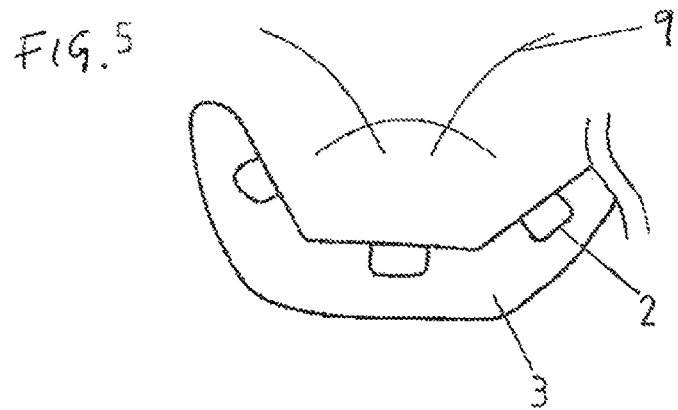
Figure 6:
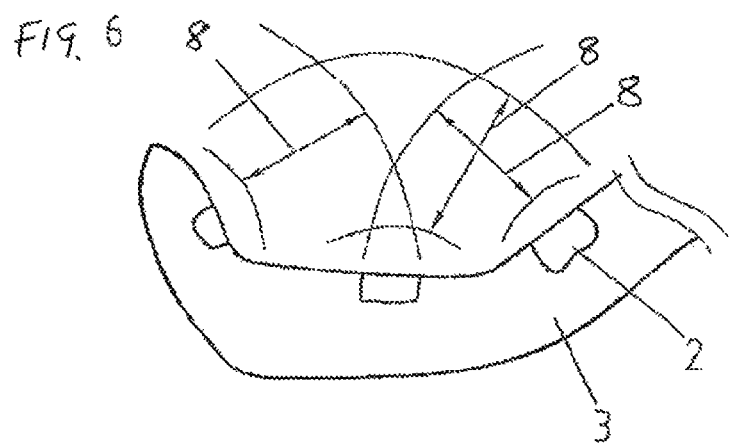

The figures show:

FIG. 1 assembled individual scan areas,

FIG. 2 an overlap area of adjacent individual scan areas,

FIG. 3 a basic representation of a scanning system,

FIG. 4 scanning surfaces in the case of the use of confocal or OCT individual scan systems, FIG. 5 scan areas with multipoint OCT or multipoint confocal imaging, FIG. 6 scan areas with chromatically dispersive confocal multipoint measurement systems, and

FIG. 7 scan areas.

The teaching according to the invention will be described using the example of a scanner for dental applications in the mouth of a patient, without implying a limitation thereby.

When scanning semitransparent objects, such as teeth or tissues, but also ceramics, etc., methods that require no coating, or at least no opaque coating of the geometry to be measured, have clear advantages for the user. Therefore, such a method should be used preferably, but not exclusively.

The individual scan optic systems can therefore be constructed preferably on the basis of the principles of multipoint OCT, multipoint confocal imaging, or multipoint confocal, with chromatic dispersion.

Such systems in the meantime have become feasible in the required dimensions, due to miniature cameras with CMOS chips having dimensions in the sub mm range (for example, AWAIBA).

The number of individual scan systems comprising each one sensor (preferably CCD or CMOS, but also InGaAs, PbS) with an optic system can here vary in the 2-1000 range, and it is preferably in the 10-100 range.

The system can contain an inertial system, for measuring the position relative to the object to be measured.

The pixel number of the individual sensors can be between 100×100 and 3000×3000.

The sensors, the electronic system to merge the data streams of the individual scan systems, a battery with inductive charging capacity, and preferably a wireless transmission as well as optionally an inertial system are integrated in a holder or a support.

To meet the hygiene requirements, a transparent cover can be moved over the scanning system proper, if disinfection by wiping is insufficient.

The data transmission is preferably wireless, but it can also occur by wired communication.

Depending on the individual scan systems used, different scanning depth ranges are covered.

In the case of the purely confocal OCT multipoint arrangement, the scan area consists preferably of a surface or of a limited depth range which is smaller than the object depth to be scanned, because in both cases a mechanical shifting of the confocal or interference surface is difficult given the required dimensions within the individual scan systems.

The required depth is reached by the fact that the measurement occurs while the support is moved relative to the object. Thus, by bringing the support closer to the object, the parts of the object that face the individual scan system are determined first. Then, the confocal/interference plane migrates to the parts of the object that are farther removed.

A correlated movement or a stopping of the support during a measurement is thus not required. Rather, an uncorrelated movement of the holder towards the object is possible, although a correlated movement or a stopping should also be determined by the invention.

The individual planes, that is the measurement planes, are assembled solely by optimized registration (matching) or also with the aid of additional position data from the optional inertial platform which can be operated together with an also optional platform in contact with the patient.

In the case of the chromatic dispersive confocal multipoint arrangement in the individual scan system, at least one depth measurement range is measurable simultaneously, so that, in the ideal case, with the exception of all individual scan systems, the geometry can be determined completely, or at least the partial depth range of the object can be determined simultaneously. As a result, the subsequent registration is facilitated.

FIG. 1 is a basic representation of the segmenting of individual scan areas which consist of individual scans that are measured, by means of sensors, referred to as third sensors, which originate from a common holder, and are thus in a fixed relation to each other. Here, one uses particularly miniature cameras having, for example, CMOS chips with dimensions in the submillimeter range, as sold by Awaiba.

The sensors or individual scan systems originating from the holder can vary in the 2-1000 range, but they are preferably in the 10-100 range The individual scan system here also comprises, besides the sensor surface, such as, CCD, CMOS, InGaAs or PbS, the optic system, wherein the optic system can be constructed for each individual sensor on the basis of the principles of multipoint OCT, multipoint confocal imaging, or multipoint confocal, with chromatic dispersion.

The number of pixels per sensor can be between 100×100 and 3000×3000.

Furthermore, one can see in FIG. 1 that, for example, a jaw of a chewing organ is recorded, wherein the occlusal area A, the vestibular area B, and the platinal or lingual area C are covered simultaneously.

FIG. 2 illustrates that the individual scans of FIG. 1 partially overlap.

One can see furthermore from FIGS. 1 and 2 that the third sensors are arranged in such a manner that the individual scans thereof abut against each other without any gaps, or they overlap at least partially, that is, in their marginal areas, to allow matching.

FIG. 3 is a basic representation of the components by means of which the individual scans which present a fixed relation to each other are determined. The system comprises 1 ... n sensors of the respective individual scan systems, a field-programmable gate array (FPGA) electronic system for merging the data streams of the individual scan systems with the sensors 1 ... n, preferably an inertial system to make available motion data if any as well as components for the data transmission to a PC for the calculation of the geometry. The PC can also be used as user interface. From the basic representation, one can see that the data transmission can be by wired communication or wireless.

The individual scan systems with the electronic system start from a common holder 2, which can also be referred to as support (FIG. 4). In the holder 2, the individual scan systems 7 are integrated. Furthermore, a battery 4 and optionally a coil 5 for an inductive charging system for the battery 4 are provided. Moreover, an inertial system can optionally be arranged next to the electronic system 3. The corresponding arrangement is here designed geometrically, in reference to the sensors 1 ... n or the individual scan systems 1 ... n, in such a manner that a jaw area 6 to be measured is at least partially enclosed, to consequently measure the total individual scan areas that can be seen in FIG. 1.

To the extent that the individual scan systems are constructed according to the principle of multipoint OCT or multipoint confocal imaging, one gets the scan surfaces 9 according to FIG. 5. Reference 2 marks the individual scan systems and 3 the holder.

In the case of a chromatic dispersive confocal multipoint measurement system for the individual measurement systems, the result is a depth scan area 8 which can be seen in FIG. 6. The individual scan systems are again marked with reference 2 and the holder or support with 3.

According to the teaching of the invention, individual scans can also be used without fixed assignment to each other, for the determination of the total data of a total data set. For this purpose, sensors referred to as first sensors are used, which are arranged in a first apparatus. In order to assign the individual scans to each other, or in order to subject a total data set calculated therefrom to rectification or to correction, individual, discontiguous, scan areas 8 that are in an unequivocal fixed geometric arrangement to each other are used. Said scan areas 8 are measured by means of two sensors which are arranged in a fixed relation to each other in a second apparatus.

Figure 7:
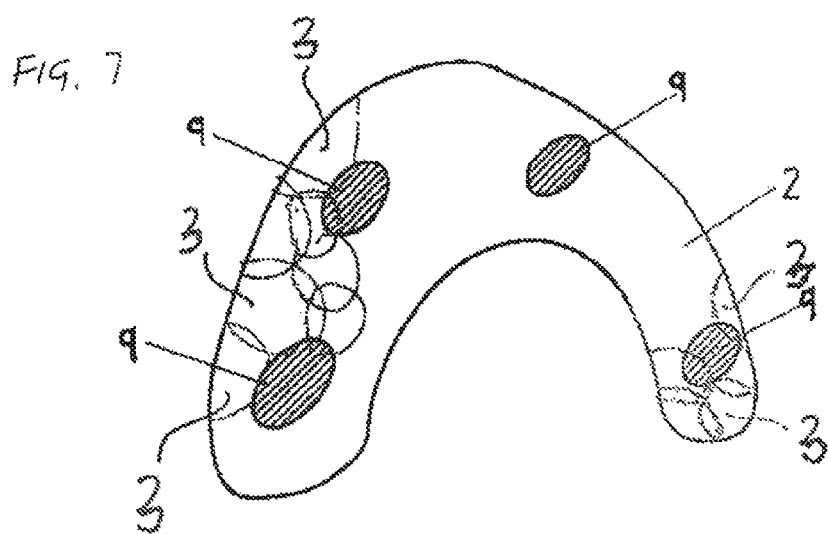

The possibility here exists to correct the scan areas 3 determined by at least a first sensor, the with the scan areas 9 (FIG. 7) which were determined by the sensors which are in a fixed relation, and which are thus in an unequivocal mutual arrangement, in order to then calculate the total data set. To calculate the total data set, the individual scans 3 must mutually overlap, and several individual scans 3 overlap the scan areas 9. In other words, due to the registration of the individual scan areas 3 to each other and to the scan areas 9, a correction of the individual scan 3 is possible.

The individual scan areas 3 can also be measured with a single sensor of an apparatus.

Alternatively and preferably, the possibility exists to first calculate, from the individual scans 3 that are not in a fixed relation, a total set for the registration of said scans, which represents the object or the area to be measured. Said total data set is then corrected taking into consideration the individual scans or scan areas 1 determined by the sensors 2 which are in a fixed relation, so that in particular accumulated errors of individual scan data, that is of the data of the areas 3, can be corrected.

The correction of the scan areas 3 by the scan areas 1, and then the calculation of the total data set from the corrected data of the scan areas 3 thus represent to that extent an equivalence to a correction of the total data set calculated from the individual scans 3.

Based on the teaching according to the invention, a 3D total data set of high accuracy is thus made available, which represents the area of the chewing organ or of the jaw 2 to be measured.

The invention claimed is:

1. A method for determining a total data set of a chewing organ, or an area thereof, the method comprising:
   providing a first sensor,
   providing at least two second sensors arranged in a fixed relation,
   carrying out first partial scans of the chewing organ, or the area thereof, using the first sensor, to measure partially overlapping areas of the chewing organ, or the area thereof,
   carrying out second partial scans of the chewing organ using the at least two second sensors,
   calculating the total data set of the chewing organ, or the area thereof, from individual data sets from the first partial scans, and either
   (a) correcting the total data set using the second partial scans, or
   (b) correcting individual data sets from the first partial scans using the second partial scans to produce corrected first partial scans, and generating the total data set of the chewing organ, or the area thereof, from the corrected first partial scans.

2. The method according to claim 1, wherein the at least two second sensors are individual scan optic systems which are constructed according to the principle of multipoint optical coherence tomography, multiple confocal imaging, or multipoint confocal imaging, with chromatic dispersion.

3. The method according to claim 1, wherein at least one of the first sensor and the at least two second sensors are selected from the group consisting of a CCD, CMOS, InGaAs and PbS senor.

4. The method according to claim 1, wherein at least one of the first sensor and the at least two second sensors are a miniature camera in the submillimeter range.

5. The method according to claim 1, wherein the optic system of the at least two second sensors has a confocal design.

6. The method according to claim 1, wherein the at least two second sensors are connected to a holder to form a unit.

7. A method for determining a total data set of a chewing organ, or an area thereof, the method comprising:
   providing a first sensor,
   providing a plurality of second sensors fixedly attached to a holder,
   determining individual data sets of partial scans of the chewing organ using the first sensor,
   determining partial scans from the individual data sets using the plurality of second sensors, and
   calculating the total data set of the chewing organ from the partial scans from the individual data sets,
   moving the plurality of second sensors in an uncorrelated manner with respect to the chewing organ,
   simultaneously scanning occlusal, vestibular, and palatinal/lingual areas of the patient's mouth, wherein the holder is displaced in the patient's mouth during the determining of the partial scans.

8. The method according to claim 7, wherein an electronic system for merging data streams of the sensors, and a voltage source, is integrated in the holder, besides the plurality of second sensors.

9. The method according to claim 8, wherein the voltage source is a battery with inductive charging capacity.

10. The method according to claim 7, wherein a transmission of the data of the plurality of second sensors is wireless.

11. The method according to claim 7, wherein the holder is covered by a transparent enveloping cover.

12. The method according to claim 7, wherein the holder is dimensioned in such a manner that an at least partial introduction into the mouth of a patient occurs.

13. A The method according to claim 7, wherein the plurality of second sensors are arranged in such a manner that the partial scans of said sensors abut against each other without any gap, or mutually overlap, at least in sections, partially in sections.

14. The method according to claim 7, wherein the at least two second sensors are individual scan optic systems which are constructed according to the principle of multipoint optical coherence tomography, multiple confocal imaging, or multipoint confocal imaging, with chromatic dispersion.

15. The method according to claim 7, wherein at least one of the first sensor and the at least two second sensors are selected from the group consisting of a CCD sensor, a CMOS sensor, an InGaAs sensor, and a PbS sensor.

16. The method according to claim 7, wherein at least one of the first sensor and the at least two second sensors is a miniature camera in the submillimeter range.

17. The method according to claim 7, wherein the optic system of the plurality of second sensors has a confocal design.

18. A device for scanning a chewing organ, or an area thereof, comprising a holder with a plurality of sensors originating therefrom, by means of which the chewing organ, or the area thereof, is scanned,
wherein the holder presents a three-dimensional geometry for the at least partial enclosure of a jaw area, and
wherein the holder further comprises an electronic system for merging data determined by the plurality of sensors, and a power source,
wherein the plurality of sensors are attached in such a manner to the holder that an occlusal, vestibular, and palatinal/lingual area of at least one area of the chewing organ can be scanned simultaneously; and
wherein the holder is configured so that the holder can partially be placed in the mouth of a patient.

19. The device according to claim 18, wherein a sensor of the plurality of sensors is selected from the group consisting of a CCD sensor, a CMOS sensor, an InGaAs sensor, a PbS sensor, and a miniature camera in the submillimeter area.

20. The device according to claim 18, wherein the holder presents an inertial system.

21. The device according to claim 18, wherein the holder is provided with a transparent enveloping cover that covers at least the plurality of sensors.

22. The device according to claim 18, wherein the holder presents a three-dimensional geometry to enclose a jaw area at least in sections.

* * * * *